United States Patent [19]

Hennig et al.

[11] 4,292,255

[45] Sep. 29, 1981

[54] PROCESS FOR THE PREPARATION OF ORGANIC POLYISOCYANATES CONTAINING UREA GROUPS

[75] Inventors: Hans J. Hennig, Leverkusen; Peter Ziemek; Erhard Schellmann, both of Cologne, all of Fed. Rep. of Germany

[73] Assignee: Bayer Aktiengesellschaft, Leverkusen, Fed. Rep. of Germany

[21] Appl. No.: 213,434

[22] Filed: Dec. 5, 1980

Related U.S. Application Data

[60] Division of Ser. No. 137,676, Apr. 7, 1980, which is a continuation of Ser. No. 3,576, Jan. 15, 1979, abandoned.

[30] Foreign Application Priority Data

Jan. 25, 1978 [DE] Fed. Rep. of Germany ....... 2803103

[51] Int. Cl.³ .............. C07C 119/042; C07C 119/045; C07C 119/048
[52] U.S. Cl. .......... 260/453 AR; 260/453 A; 260/453 AB; 260/453 AL
[58] Field of Search ................. 260/453 AL, 453 AR, 260/453 A, 453 AB

[56] References Cited

U.S. PATENT DOCUMENTS

| | | | |
|---|---|---|---|
| 3,201,372 | 8/1965 | Wagner | 260/453 AB |
| 3,903,126 | 9/1975 | Woerner et al. | 260/453 AB |
| 3,943,158 | 3/1976 | Dietrich et al. | 260/453 A |
| 4,147,714 | 4/1979 | Hetzel et al. | 260/453 AB |

FOREIGN PATENT DOCUMENTS

| | | | |
|---|---|---|---|
| 1101394 | 9/1961 | Fed. Rep. of Germany . | |
| 2261065 | 6/1974 | Fed. Rep. of Germany | 33/2 |
| 2609995 | 9/1977 | Fed. Rep. of Germany | 127/24 |
| 1263609 | 2/1972 | United Kingdom . | |

*Primary Examiner*—Dolph H. Torrence
*Attorney, Agent, or Firm*—Gene Harsh; Lawrence S. Pope; Thomas W. Roy

[57] ABSTRACT

The present invention relates to a process for the preparation of compounds selected from the group consisting of a polyisocyanate containing urea groups and a polyisocyanate containing biuret groups comprising (a) introducing an organic polyisocyanate into a reaction vessel, and
(b) injecting an organic polyamine containing at least two primary amino groups into the organic polyisocyanate in the reaction vessel at a pressure of from about 2 to 1000 bar through a straight jet nozzle having an internal diameter of from about 0.01 to 5 mm wherein (i) the polyisocyanate/polyamine $NCO/NH_2$ molar ratio is at least about 4:1 and
(ii) the temperature in the reaction vessel is between about $-20°$ C. to $250°$ C.

7 Claims, 2 Drawing Figures

PROCESS FOR THE PREPARATION OF ORGANIC POLYISOCYANATES CONTAINING UREA GROUPS

This application is a division of application Ser. No. 137,676, filed Apr. 7, 1980, which itself is a continuation of application Ser. No. 3,576, filed Jan. 15, 1979, now abandoned.

FIELD OF THE INVENTION

This invention relates to an improved process for the preparation of polyisocyanates containing biuret and/or urea groups, by the reaction of organic polyisocyanates with less than equivalent quantities of organic polyamines.

BACKGROUND OF THE INVENTION

It is already known to react low molecular weight organic polyisocyanates with low molecular weight organic polyamines to produce both ureas and biurets but, owing to the extremely high reactivity of isocyanate groups towards primary amino groups, the reaction from the said low molecular weight starting materials has not become established in large scale industrial processes, apart from a few exceptions. The main reason for this is that, in reactions carried out on a large scale, the extremely high reactivity of the aforesaid groups makes it virtually impossible to control the reaction to produce clearly defined end products.

The production of biuret polyisocyanates on an industrial scale has, therefore, hitherto preferably been carried out by the reaction of organic diisocyanates with so-called "biuretizing agents", i.e. compounds such as water, for example, which first react with isocyanate groups to form amino groups, this initial reaction then being followed by the biuretization reaction between the amine which has been formed in situ and the excess isocyanate as described in German Pat. No. 1,101,394 and U.S. Pat. No. 3,201,372. Since amino groups are never present in significant concentrations in this process, the undesirable side reactions due to the high reactivity do not occur.

Another method of overcoming the difficulties due to the high reactivity has been described in British Pat. No. 1,263,609. In this case, the diisocyanates are not reacted with free diamines but instead, the concentration of the highly reactive amino groups is reduced by the addition of carbonyl compounds to the amines.

The direct reaction between low molecular weight diprimary diamines and low molecular weight diisocyanates to produce the corresponding biuret polyisocyanates has been described in German Offenlegungsschrift No. 2,261,065 and U.S. Pat. No. 3,903,126. When the examples given in this publication were repeated, however, it was found that only the particular diamines described as preferred were suitable for the preparation of commercially usable biuret polyisocyanates, whereas the most important aliphatic diamine, hexamethylene diamine, could not be converted into a light colored biuret polyisocyanate free from sedimentation by the process according to German Offenlegungsschrift No. 2,261,065 and U.S. Pat. No. 3,903,126, in particular when it was used in combination with hexamethylene diisocyanate.

Although the process according to German Offenlegungsschrift No. 2,609,995 and U.S. Pat. No. 4,147,714, makes it possible for such light colored, sedimentation-free, biuret polyisocyanates to be prepared by the direct reaction of hexamethylene diamine with hexamethylene diisocyanate, the process described in this publication has the disadvantage that the diamine must be introduced in the gaseous state into the diisocyanate, which complicates the procedure.

The reaction between organic polyisocyanates, in particular diisocyanates, with diprimary organic diamines to produce the corresponding urea isocyanates has not in any way become established as an industrial process. In the above mentioned publications, the formation of such urea isocyanates is merely mentioned as an undesirable side effect of the preparation of biuret polyisocyanates, and no one has yet succeeded in finding a technically feasible method of utilizing the direct reaction between diprimary organic diamines and excess quantities of low molecular weight organic diisocyanates to produce the corresponding polyisocyanates containing urea groups.

The process according to the present invention described below for the first time discloses a method for reacting any organic compound containing at least two primary amino groups directly with any organic polyisocyanate to form the corresponding polyisocyanate containing urea groups or biuret groups without having to use special diamines or special auxiliary agents, for example ketones, or having to introduce the diamine in a gaseous form.

In the process according to the invention described below, the reaction can be simply controlled by suitable choice of the reaction temperature to produce either solutions of the corresponding biuret polyisocyanates in excess polyisocyanate or sedimentation-resistant, dispersions of the corresponding urea polyisocyanates in excess polyisocyanate, as desired.

The process according to the invention therefore not only provides a very simple means of preparing known biuret polyisocyanates such as those based on hexamethylene diamine and hexamethylene diisocyanate, for example, but also for the first time provides the possibility of preparing commercially, highly interesting, dispersions of urea diisocyanates in excess diisocyanate. Sedimentation resistant dispersions of this type have not hitherto been known. They constitute particularly interesting starting materials for the polyurethane chemist.

SUMMARY OF THE INVENTION

The present invention relates to a process for the preparation of polyisocyanates containing urea groups and/or biuret groups in the form of dispersions or solutions in polyisocyanates which are free from urea and biuret groups by the reaction of organic polyisocyanates with organic polyamines containing at least two primary amino groups at an NCO/NH$_2$ molar ratio of at least about 4:1. In carrying out the reaction, the polyisocyanate used in excess, which serves both as reactant and as solvent or dispersing agent, is first introduced into the reaction vessel and the polyamine, which is used in less than the equivalent quantity, is introduced into the polyisocyanate at a temperature within the range of from about −20° C. to 250° C. The process is characterized in that (a) the polyisocyanate component which is used in excess is first introduced into a reaction vessel and (b) the polyamine component, used in less than the equivalent quantity, is injected into the polyisocyanate component at a pressure of from about 2 to 1000 bar, using a straight jet nozzle having an internal diameter of about from 0.01 to 5 mm.

DETAILED DESCRIPTION OF THE INVENTION

Figure 1:
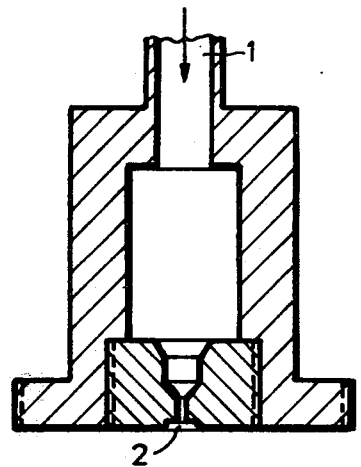
FIG. 1 illustrates a straight jet nozzle suitable for use in the process according to the invention. It indicates at
(1) the inlet to the nozzle and at
(2) the straight jet nozzle proper.

Any organic polyisocyanates may be used as a starting material for the process according to the invention, but organic diisocyanates are preferably used. Suitable diisocyanates are in particular those corresponding to the formula $$R_1(NCO)_2$$

in which $R_1$ represents an aliphatic hydrocarbon group having from 2 to 18 carbon atoms, an aromatic hydrocarbon group having from 6 to 15 carbon atoms, an araliphatic hydrocarbon group having from 8 to 15 carbon atoms or a cycloaliphatic hydrocarbon group having from 4 to 15 carbon atoms, at least two carbon atoms being situated in each case between the two isocyanate groups.

The following are examples of such diisocyanates: ethylene diisocyanate; hexamethylene diisocyanate; decamethylene diisocyanate; undecamethylene diisocyanate; octadecamethylene diisocyanate; 3,3,5-trimethyl-1,6- diisocyanatohexane; p-phenylenediisocyanate; 2,4-diisocyanatotoluene; 2,6-diisocyanatotoluene, 4,4'-diisocyanatodiphenylmethane; 2,4'-diisocyanatodiphenylmethane; mixtures of the last two mentioned isomers with their higher nuclear homologues such as are obtained from the known process of phosgenating aniline/formaldehyde condensates; p-xylylenediisocyanate; cyclobutane-diisocyanate-(1,3); 1,4-diisocyanatocyclohexane; 1methyl-2,4-diisocyanatocyclohexane; 4,4'-diisocyanatodicyclohexylmethane; 3,3,5-trimethyl-5-isocyanatomethyl-cyclohexylisocyanate (IPDI) and mixtures of these diisocyanates.

Preferred diisocyanates for the process according to the invention are: 2,4-diisocyanatotoluene; commercial mixtures thereof with 2,6-diisocyanatotoluene; 4,4'-diisocyanatodiphenylmethane; commercial mixtures thereof with 2,4'-diisocyanatodiphenylmethane; hexamethylene diisocyanate and IPDI. The above mentioned diisocyanatotoluenes and hexamethylenediisocyanate are particularly preferred.

The organic polyamine reactants used for the polyisocyanates exemplified above may be any organic compounds which have at least two primary amino groups. Apart from the amino groups, they are preferably inert towards isocyanate groups. For the process according to the invention, it is particularly preferred to use diprimary diamines corresponding to the formula $$R_2(NH_2)_2$$

in which $R_2$ may be the same as or different from $R_1$, but conforms to the definition of $R_1$.

Particularly suitable diamines for the process according to the invention are those which correspond to the diisocyanates mentioned as examples.

The following are preferred diamines for the process according to the invention: 2,4-diaminotoluene and its commercial mixtures with 2,6-diaminotoluene; 4,4'-diaminodiphenylmethane and its commercial mixtures with 2,4'-diaminodiphenylmethane; hexamethylene diamine; 4,4'-diaminodicyclohexylmethane and its homologues and 3,3,5-trimethyl-5-aminomethyl-cyclohexylamine (IPDA). The above mentioned diaminotoluenes, diaminodiphenylmethanes and hexamethylenediamine are particularly preferred.

One essential feature of the invention is the use of a particular nozzle in combination with a particular reaction vessel. The process according to the invention is carried out using straight jet nozzles having a diameter of from about 0.01 to 5 mm, preferably from about 0.1 to 1 mm, and the isocyanate component, which is used in excess, is first introduced into the reaction vessel and the amine component, which is used in less than the equivalent quantity, is injected into the isocyanate component in the reaction vessel.

It is preferred that the injected amine component enters the isocyanate component already in the reaction vessel at a relative velocity of at least about 5 m/sec and that the reaction vessel be of such dimensions that the distance from the nozzle to the wall of the reaction vessel opposite the nozzle measured in the direction of the injection jet, is at least about 100 times the diameter of the nozzle while the smallest lateral distance from the jet to the internal wall of the reaction vessel is at least about 25 times the diameter of the nozzle.

When carrying out the process according to the invention, it is also preferred that the pressure in the reaction vessel is always greater than the vapor pressure of the most volatile component in the mixture under the given temperature conditions so that no bubbles of vapor or gas will form in the reaction vessel. The component which is to be injected is generally injected at a pressure of from about 2 to 1000 bar, preferably from about 10 to 200 bar. The formation of an unwanted gas space at the outlet of the nozzle and in the mixing zone can also be prevented by injecting in an upwardly direction from the bottom of the reaction vessel because in this way any gas bubbles which may form in spite of the selected pressure conditions would escape upwards out of the mixing zone.

Figure 2:
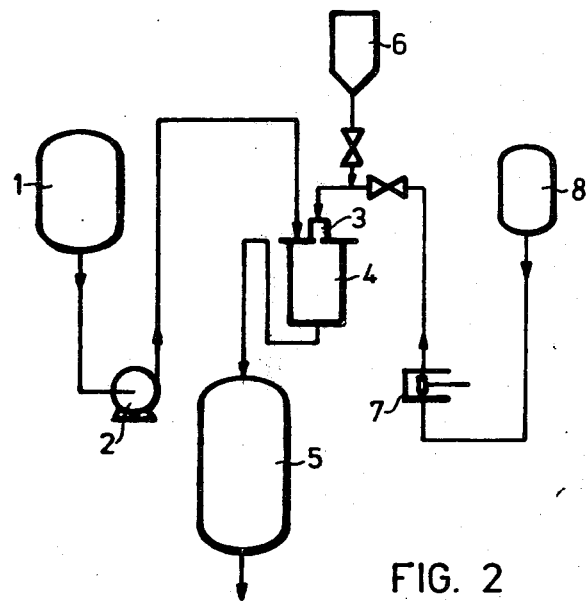
FIG. 2 represents a possible apparatus for carrying out the process according to the invention continuously, which comprises the following parts:
(1) a storage container for the isocyanate component,
(2) a pump for the isocyanate,
(3) the nozzle,
(4) the reaction vessel,
(5) the storage container for the end product,
(6) the storage container for a rinsing liquid,
(7) a high pressure pump and
(8) a storage vessel for the amine component.

If the process according to the invention is carried out as a continuous process in an apparatus as shown in FIG. 2, it is advisable to build up the full operating pressure at the beginning of the process, before the reactants are brought together, so that the desired outflow velocity is reached at the very beginning of the reaction according to the invention. To achieve this, it has been found advantageous to fill the feed pipe to the straight jet nozzle with an inert liquid before high pressure injection is begun so that the only substance leaving the nozzle during the time required for building up the pressure to the operating pressure is an inert liquid.

When carrying out the process according to the invention, the starting materials are reacted together in an NCO/NH$_2$ equivalent ratio of from about 4:1 to 1000:1, preferably from about 5:1 to 25:1. When the process according to the invention is carried out continuously, the quantity of reactants continuously introduced into the reaction vessel corresponds to the preselected equivalent ratio within the ranges indicated above. If the process is carried out batchwise, as is also possible, the total quantity of isocyanate component is introduced into a suitable reaction vessel, for example a tank, and the nozzle dips into the liquid in the reaction vessel.

By simple choice of the starting components and the reaction temperature, the process according to the invention can be controlled to produce either sedimentation resistant dispersions of urea group-containing diisocyanates in excess starting isocyanate or solutions of biuret group-containing polyisocyanates in excess starting isocyanate. Thus, the process according to the invention results in finely dispersed urea dispersions having an average particle size of about 0.5 to 250 μm if the temperature in the reaction vessel is kept below the melting point of the urea which is always originally formed from the isocyanate and amine.

The preparation of solutions of polyisocyanates containing biuret groups in excess starting isocyanate may either be carried out in two stages by reheating the urea dispersions originally formed at a relatively low temperature or it may be carried out by adjusting the temperature in the reaction vessel even while carrying out the process according to the invention, so that the urea initially formed is directly obtained as a liquid which is soluble in the starting isocyanate and reacts with the excess isocyanate to form a polyisocyanate containing biuret groups without the intermediate formation of urea being visible macroscopically at all. The temperature which must be maintained in the reaction vessel during the process according to the invention in order to obtain dispersions of polyisocyanates containing urea groups or solutions of polyisocyanates containing biuret groups in excess starting isocyanate may vary within the wide limits of from about −20° C. to 250° C., depending on the nature of the chosen starting materials, and can easily be determined reliably by a preliminary test.

The process according to the invention is of particular interest for the preparation of dispersions of urea polyisocyanates based on aromatic diisocyanates and aromatic diamines in excess aromatic diisocyanate and for the preparation of biuret polyisocyanates containing aliphatically bound isocyanate groups from aliphatic diisocyanates and aliphatic diamines.

The process according to the invention is particularly suitable for the preparation of dispersions of urea group-containing diisocyanates in 2,4-diisocyanatotoluene or in commercial mixtures thereof with 2,6-diisocyanatotoluene. To prepare these dispersions, the last mentioned diisocyanatotoluenes are introduced into the reaction vessel as starting isocyanate and preferably 2,4-diaminotoluene or commercial mixtures thereof with 2,6-diaminotoluene or some other aromatic diamine, e.g. 4,4'-diaminodiphenylmethane or commercial mixtures thereof with 2,4'-diaminodiphenylmethane and/or its higher homologues is used as the amine component. The reaction according to the invention is preferably carried out in the region of from about 20° to 120° C. The temperature is adjusted by suitable choice of the diisocyanate component and its temperature, taking into account the heat of reaction and the temperature of the injected diamine component.

Since the diisocyanate component is always present in excess in the reaction according to the invention and since, even when mixtures of 2,4- and 2,6-diisocyanatotoluene are used, it may be assumed that the isocyanate group which is in the para-position to the methyl group in 2,4-diisocyanatotoluene reacts preferentially, the reaction according to the invention preferentially gives rise to urea diisocyanates corresponding to the following formula, which are not chain lengthened:

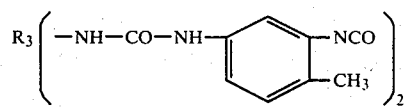

in which R$_3$ represents a divalent aromatic hydrocarbon group obtained by removal of the amino group which may carry methyl substituents or methylene bridges forming a diphenylmethane structure and has a total of from 6 to 15 carbon atoms.

In accordance with the particulars given above, R$_3$ is preferably a group obtained by removal of the amino groups from 2,4-diaminotoluene or from commercial mixtures thereof with 2,6-diaminotoluene or from 4,4'-diaminodiphenylmethane or commercial mixtures thereof with 2,4'-diaminodiphenylmethane. When using mixtures of 4,4'-diaminodiphenylmethane (and optionally 2,4'-diaminodiphenylmethane) with higher polyamines of the diphenylmethane series, such as are obtained on a large commercial scale as products of the known aniline/formaldehyde condensation, urea diisocyanates corresponding to the above formula are obtained side by side with higher functional urea polyisocyanates which correspond to the higher homologues in their functionality.

The dispersions of urea diisocyanates corresponding to the last mentioned formula which are produced in the process according to the invention may be regarded as modified tolylene diisocyanates, for which there are possibilities of numerous extremely interesting fields of application. The proportions of materials used for the preparation of these dispersions are generally chosen so that about 5 to 40% by weight dispersions of the urea diisocyanates in excess diisocyanatotoluene are formed, i.e. an NCO/NH$_2$ equivalent ratio of about 50:1 to 5:1 is preferably employed.

The process according to the invention is also particularly suitable for the preparation of polyisocyanates which contain biuret groups or solutions of these polyisocyanates in excess aliphatic diisocyanate. The starting materials used for preparing such products by the process according to the invention are preferably diisocyanates corresponding to the formula $$R_1(NCO)_2$$

in which

R$_1$ represents a polymethylene group having from 4 to 11 carbon atoms, preferably a hexamethylene group.

The diamine component used in the process according to the invention for the preparation of polyisocyanates containing biuret groups preferably consists of diamines corresponding to the following formula $$R_2(NH_2)_2$$

in which $R_2$ may be the same as or different from $R_1$ and is also a polymethylene group having from 4 to 11 carbon atoms, preferably a hexamethylene group.

As already mentioned above, the polyisocyanates containing biuret groups may be prepared either by a two-stage process, i.e. preparation of the corresponding urea dispersion as intermediate product and its thermal after-treatment, or by a one-stage process if suitably elevated temperatures are employed. When polyisocyanates containing biuret groups are prepared on the two-stage principle, the starting materials exemplified above are preferably reacted in an $NCO/NH_2$ equivalent ratio of from about 25:1 to 8:1 at a reaction temperature preferably maintained at about 50° to 180° C. The resulting urea dispersion, which incidentally may also be used for other purposes, for example as a modified aliphatic diisocyanate, may then be converted into a light-colored, sedimentation-free solution of the corresponding biuret group-containing polyisocyanate in excess diisocyanate by heating to about 150° to 250° C. Such a solution is formed directly in the process according to the invention without macroscopically detectable intermediate formation of the aforesaid urea dispersion if a reaction temperature of about 180° to 250° C. is maintained. The corresponding biuret polyisocyanates free from monomers are then obtained by removal of the excess diisocyanate by distillation or extraction. These biuret polyisocyanates, as is well known, are extremely valuable starting materials for the manufacture of polyurethane lacquers.

The process according to the invention is not, of course, limited to the preparation of those urea dispersions and biuret solutions which have been described as particularly preferred but is also suitable, for example, for the preparation of solutions of biuret group-containing isocyanates which have aromatically bound isocyanate groups. The same principles are then employed and the temperature required, depending on whether a one-stage process or a two-stage process is to be employed, must be determined by a brief preliminary test.

As already briefly outlined above, the reaction temperature is a function both of the temperature of the isocyanate component and of the temperature of the amine component, which in many cases has to be melted before the process according to the invention is carried out, as well as a function of the heat evolved in the exothermic reaction according to the invention.

The following Examples serve to explain the process according to the invention in more detail.

EXAMPLES

Example 1

In an apparatus as shown in FIG. 2, 2000 l/h of hexamethylene diisocyanate preheated to 100° C., are continuously delivered from a storage container (1) into a cylindrical reaction vessel (4) having an internal diameter of 10 cm and a length of 30 cm by a pump (2) under a pressure of 1.5 bar. At the same time, 80 kg/h of hexamethylenediamine preheated to 60° C. are injected at a pressure, in front of the nozzle, of 80 bar into the center of the mixing chamber by means of a straight jet nozzle (3) which has a diameter of 0.5 mm. The contents of the reaction vessel spontaneously heat up to 140° C. and a finely divided dispersion of the urea diisocyanate corresponding to the starting materials in excess hexamethylene diisocyanate forms instantly and spontaneously. The dispersion is continuously discharged into the storage vessel (5). The average particle size of the dispersed urea diisocyanate is 15 μm. The dispersion shows no tendency to form a sediment at room temperature, even when left to stand for 10 days. When the dispersion is heated to 180° C. for one hour, a clear solution of the corresponding biuret group-containing polyisocyanate in excess hexamethylene diisocyanate is obtained.

Example 2

Using the same apparatus as in Example 1, an isomeric mixture of 70 parts of weight of 4,4'- and 30 parts by weight of 2,4'-diaminodiphenylmethane which has previously been heated to 100° C. is reacted at a pressure of 80 bar with an isomeric mixture of 65 parts by weight of 2,4- and 35 parts by weight of 2,6-diisocyanatotoluene which has been heated to 35° C. The reaction is carried out using a proportion of diaminodiphenylmethane to diisocyanatotoluene of 3.3 to 96.7% by weight, which corresponds to a molar ratio of 1:33.7. The total rate of throughput is 2466 kg/h. A finely divided polyurea dispersion in excess diisocyanatotoluene is obtained. It has a solid content of 9% and is distinguished by its thixotropic properties. The calculated isocyanate content is 45.3%; found 45.2%.

When this dispersion is heated to 140° C. for 30 minutes a clear biuret-containing solution which has an isocyanate content of 44.2% (calculated 43.9%) is obtained.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of polyisocyanates containing urea groups comprising
   (a) introducing an organic polyisocyanate of the formula $$R_1(NCO)_2$$

wherein
   $R_1$ is an aliphatic hydrocarbon group having from 2 to 18 carbon atoms, an aromatic hydrocarbon group having from 6 to 15 carbon atoms, an araliphatic hydrocarbon group having from 8 to 15 carbon atoms or a cycloaliphatic hydrocarbon group having from 4 to 15 carbon atoms, at least two carbon atoms in each hydrocarbon group being situated between the two isocyanate groups, into a reaction vessel, and
   (b) injecting an organic polyamine of the formula $$R_2(NH_2)_2$$

wherein
   $R_2$ is an aliphatic hydrocarbon group having from 4 to 11 carbon atoms or an aromatic hydrocarbon group having from 6 to 15 carbon atoms, into the organic polyisocyanate in the reaction vessel at a pressure of from about 2 to 1000 bar through a straight jet nozzle having an internal diameter of from about 0.01 to 5 mm
   wherein (i) the polyisocyanate/polyamine $NCO/NH_2$ molar ratio is at least about 4:1, and
(ii) the temperature in the reaction vessel is between about 20° C. to 180° C.

2. A process for the preparation of a polyisocyanate containing urea groups comprising
 (a) introducing an organic polyisocyanate of the formula $$R_1(NCO)_2$$

wherein
 $R_1$ is an aromatic hydrocarbon group having from 6 to 15 carbon atoms, into a reaction vessel, and
 (b) injecting an organic polyamine of the formula $$R_2(NH_2)_2$$

wherein
 $R_2$ is an aliphatic hydrocarbon group having from 4 to 11 carbon atoms or an aromatic hydrocarbon group having from 6 to 15 carbon atoms, into the organic polyisocyanate in the reaction vessel at a pressure of from about 2 to 1000 bar through a straight jet nozzle having an internal diameter of from about 0.01 to 5 mm
wherein
 (i) the polyisocyanate/polyamine $NCO/NH_2$ molar ratio is at least about 4:1,
 (ii) the temperature in the reaction vessel is between about 20° C. to 180° C.

3. The process of claim 2, wherein the polyisocyanate containing urea groups is prepared as a dispersion in the excess organic polyisocyanate.

4. The process of claim 2, wherein the $NCO/NH_2$ molar ratio is between about 4:1 and 1000:1.

5. The process of claim 2, wherein the $NCO/NH_2$ ratio is between about 5:1 and 25:1.

6. The process of claim 2, wherein
 (a) the distance from the nozzle to the wall of the reaction vessel opposite the nozzle measured in the direction of the injection jet is at least about 100 times the diameter of the nozzle,
 (b) the smallest lateral distance from the injection jet to an internal wall of the reaction vessel is at least about 25 times the diameter of the nozzle, and
 (c) the polyamine is injected into the polyisocyanate in the reaction vessel at a relative velocity of at least 5 m/sec.

7. A process for the preparation of polyisocyanates containing urea groups dispersed in polyisocyanates which are free from urea and biuret groups, by the reaction of organic diisocyanates of the formula $$R_1(NCO)_2$$

wherein
 $R_1$ is an aromatic hydrocarbon group having from 6 to 15 carbon atoms, with organic polyamines of the formula $$R_2(NH_2)_2$$

wherein
 $R_2$ is an aliphatic hydrocarbon group having from 4 to 11 carbon atoms or an aromatic hydrocarbon group having from 6 to 15 carbon atoms, using an $NCO/NH_2$ molar ratio of at least about 4:1, the polyisocyanate used in excess, which serves both as reactant and solvent, being first introduced into the reaction vessel, whereas the polyamine, which is used in less than the equivalent amount, is introduced into the polyisocyanate in the reaction vessel at a temperature in the range from about 20° to 180° C., characterized in that
 (a) the polyisocyanate component, which is used in excess, is first introduced into the reaction vessel;
 (b) the polyamine component, which is used in less than the equivalent quantity, is injected at a pressure of from about 2 to 1000 bar into the polyisocyanate component in the reaction vessel at a relative velocity of at least about 5 m/sec by means of a straight jet nozzle which has an internal diameter of from about 0.01 to 5 mm; and
 (c) the dimensions of the reaction vessel are chosen so that the distance from the nozzle to the internal wall of the reaction vessel measured in the direction of the injection jet is at least about 100 times the diameter of the nozzle, and the shortest distance from the nozzle jet to the lateral wall of the reaction vessel is at least about 25 times the diameter of the nozzle.

* * * * *